United States Patent [19]
DiLeo et al.

[11] Patent Number: 5,017,292
[45] Date of Patent: May 21, 1991

[54] MEMBRANE, PROCESS AND SYSTEM FOR ISOLATING VIRUS FROM SOLUTION

[75] Inventors: Anthony J. DiLeo, Westford; Anthony E. Allegrezza, Jr., Milford; Edmund T. Burke, Winchester, all of Mass.

[73] Assignee: Millipore Corporation, Bedford, Mass.

[21] Appl. No.: 521,784

[22] Filed: May 10, 1990

[51] Int. Cl.$^5$ .............................................. B01D 16/14
[52] U.S. Cl. ...................................... 210/645; 210/654; 210/500.36; 210/500.42
[58] Field of Search ................ 210/634, 644, 645–647, 210/649–654, 500.21, 500.22, 500.27, 500.36, 500.42

[56] References Cited

U.S. PATENT DOCUMENTS 4,473,474  9/1984  Ostreicher et al. .................. 210/636
4,673,504  6/1987  Ostreicher et al. ............ 210/500.37
4,708,803  11/1987  Ostreicher et al. .................. 210/650

*Primary Examiner*—Frank Sever
*Attorney, Agent, or Firm*—Andrew T. Karnakis; Paul J. Cook

[57] ABSTRACT

A composite membrane and process utilizing the membrane which is capable of selectively removing particles such as viral particles from a solution such as a protein solution is provided. The membrane comprises a porous membrane substrate, a surface skin having ultrafiltration separation properties and an intermediate porous zone between the substrate and the skin which intermediate zone has an average pore size smaller than that of the substrate. The intermediate zone is free of voids which break the skin and which directly fluid communicate with the substrate. The composite is capable of a log reduction value of at least 3 (99.9% removal) of particles selectively from solution.

20 Claims, 10 Drawing Sheets

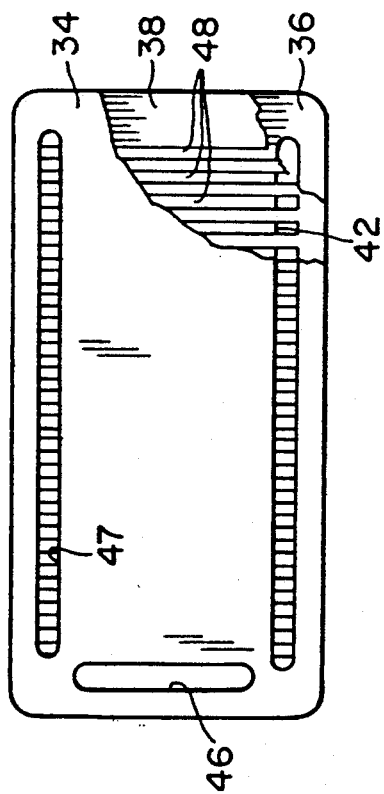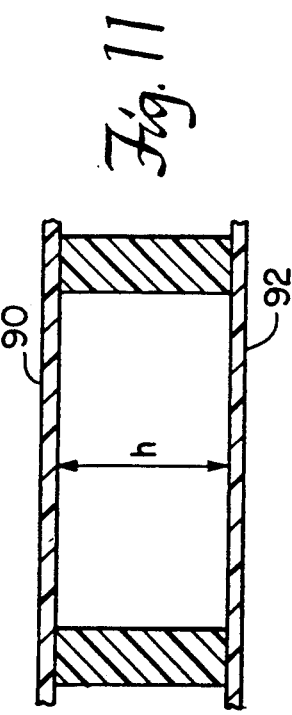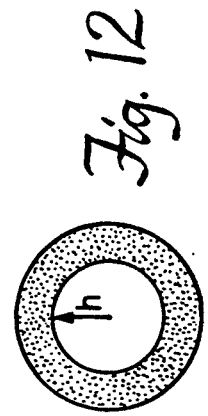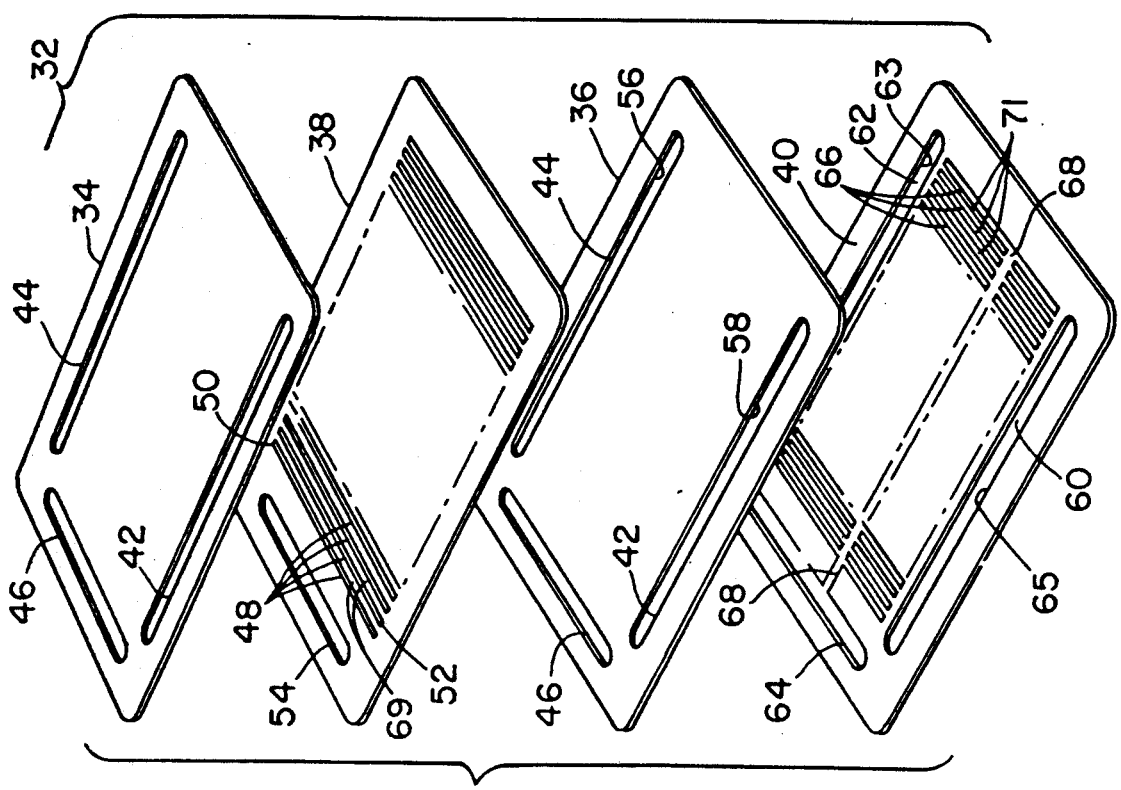

MEMBRANE, PROCESS AND SYSTEM FOR ISOLATING VIRUS FROM SOLUTION

BACKGROUND OF THE INVENTION

This invention relates to a membrane, process and system for removing particles such as virus particles from solutions such as aqueous protein solutions effectively, selectively and reproducibly. More specifically, this invention relates to a composite asymmetric membrane having a specific microstructure which is useful in a process or system for removing virus at a log retention value of between about 3 and 8, i.e., about 99.9 to 99.999999% removal of particles from solution.

Virus represent a potential contaminant in parenteral and other solutions containing a protein which are derived from either whole organisms or mammalian cell culture sources. Currently several chemical and physical methods exist to inactivate virus. These methods are not generic to all virus equally and some operate at the expense of protein activity. For example, heat pasteurization is used in solutions where protein denaturization can be minimized through the addition of stabilizers. In the biotechnology industry, strategies have been adopted that combine several inactivation or removal steps in the downstream process to maximize virus removal capability and protein recovery. The operations used are generally those operations optimized to purify the parenteral product and are validated for their virus removal capability. Thus, virus removal is a by-product of normal operation. Finally, at the end of the process, steps such as chromatography, filtration or heat may be added to increase overall virus clearance. This strategy has two shortcomings; (1) the virus clearance of these operations may not apply to putative virus that cannot be assayed; and (2) the virus clearance of the process needs to be monitored continually.

Ultrafiltration membranes have been proposed to separate virus from protein in solution. The ideal membrane would retain virus on the basis of its size and allow smaller proteins to pass. Indeed, ultrafiltration membranes are used in the biotechnology industry for this purpose. However, present asymmetric ultrafiltration membranes lack the resolution and reproducibility to perform an optimized virus-protein separation. Typically, asymmetric ultrafiltration membranes that are porous enough to pass economically useful percentages of protein, lack the consistency and high level of virus retention to obtain optimum performance that does not require continuous monitoring and revalidation.

U.S. Pat. No. 4,808,315 describes a hollow fiber membrane with a unique pore structure that is useful in the removal of virus from protein solutions. The membrane is not an asymmetric skinned ultrafilter possessing a surface retention mechanism. Rather it retains virus particles within its structure. It is described as a novel porous hollow fiber membrane which is characterized by such a unique porous structure that the inner and outer membrane surfaces have an in-a-plane average pore diameter of 0.01 to 10 microns and the porous membrane wall has an in-a-plane porosity of not less than 10% measured in every plane perpendicular to a radial direction of the annular cross-section of the hollow fiber membrane, wherein the in-a-plane porosity exhibits at least one minimum value between the inner and outer membrane surfaces.

U.S. Pat. No. 4,824,568 discloses a process for forming an asymmetric skinned membrane on a porous support. The patent does not disclose whether the membrane is useful for the selective removal of virus from a protein-containing solution, nor does it disclose what modifications would be required to obtain a microstructure useful for reproducibly and selectively removing virus particles from protein-containing solutions.

An asymmetric ultrafiltration membrane system that can recover more than 95% of commercially significant proteins and can be validated having a log reduction value of at least about 3 logs of virus particles on the basis of size (retention increasing monotonically as a function of virus particle size) would offer a significant improvement over those available commercially today. This membrane and the system utilizing the membrane could then be used confidently to remove putative virus of any size reproducibly and conveniently without the need for costly monitoring and revalidation.

In addition, such a membrane could be utilized in other applications where it is desired to remove small particles from solution such as in the electronics industry.

SUMMARY OF THE INVENTION

The present invention is based upon the discovery that a particular asymmetric composite membrane structure having a skin possessing ultrafiltration separation properties, a porous substrate and a porous intermediate zone is particularly useful for selectively isolating virus from a protein-containing solution. The thickness of the intermediate zone is larger than a thickness where the intermediate zone becomes collapsed or nonuniform and smaller than that where voids typical of ultrafiltration membranes are formed. The membrane is formed by casting a polymer solution containing between about 10 and 21% polymer onto a microporous membrane. The cast polymer solution then is converted to a porous ultrafiltration skin and a porous intermediate zone by immersing the coated membrane into a liquid which is miscible with the solvent component of the polymer solution but is a non-solvent for the polymer component of the polymer solution. Proper selection of the immersion liquid and temperature is important to obtain the combination of high virus retention and high protein passage. The ultrafiltration skin and intermediate zone are characterized by small pores which provide a molecular weight cut off of between about $5 \times 10^2$ and $5 \times 10^6$ Daltons. By the term "cut-off" as used herein is meant at least 90% removal of species having a molecular weight at or higher than the stated cut-off molecular weight. The intermediate zone is free of voids which form a break in the skin and which cause fluid to communicate directly with the porous substrate. The coating concentration in the polymer solution coating and the coating thickness is controlled so that the thickness of the final dry intermediate zone is porous and is free of voids which extend from the skin to the membrane substrate. It has been found that the composite membranes produced by this process having an intermediate zone which is free of voids normally found in ultrafiltration membranes, are uniquely capable of selectively isolating a virus by filtration from a protein-containing solution with selectivity and reproducibility higher than that obtained via conventional membrane casting techniques.

BRIEF DESCRIPTION OF THE FIGURES

FIG. 9 is an exploded view of an ultrafiltration unit which is utilized in Example III.

FIG. 10 is a top view of an ultrafiltration unit and the first spacer of FIG. 7.

FIG. 11 is a cross-sectional view of a rectangular channel of the apparatus of FIGS. 7 and 8.

FIG. 12 is a cross-sectional view of an ultrafiltration hollow fiber which can be utilized in the present invention.

DESCRIPTION OF SPECIFIC EMBODIMENTS

Figure 1:
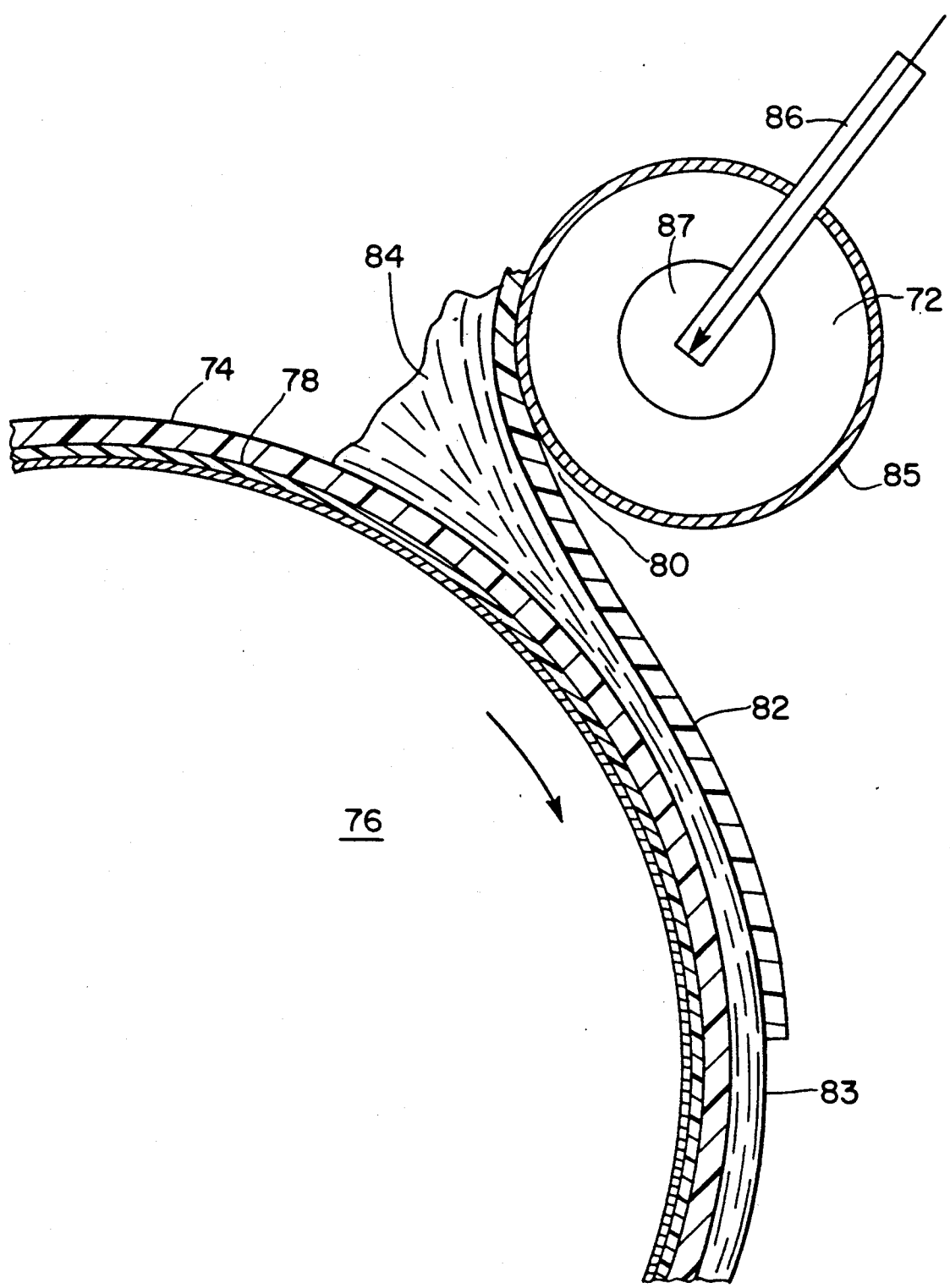
FIG. 1 illustrates the coating step employed in the present invention.
Figure 2A:
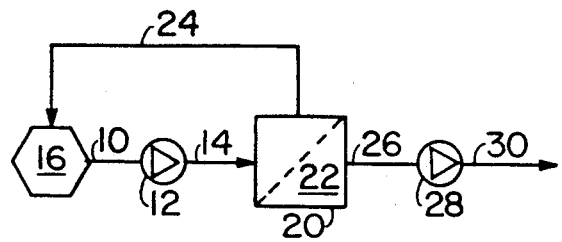
FIGS. 2a, 2b, 2c, 2d and 2e are schematic diagrams of alternative separation systems of this invention.
Figure 2B:
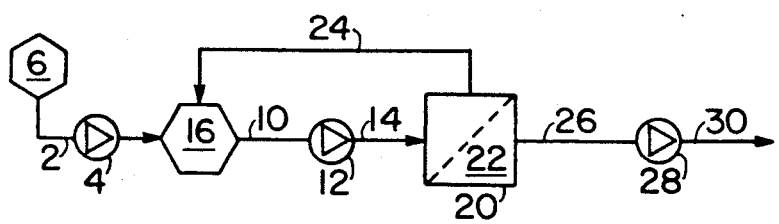
Figure 2C:
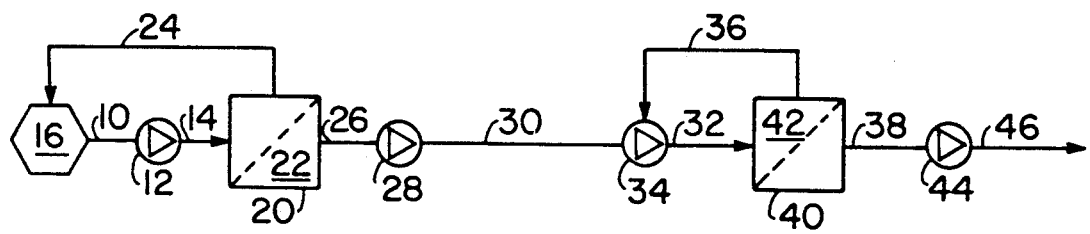
Figure 2D:
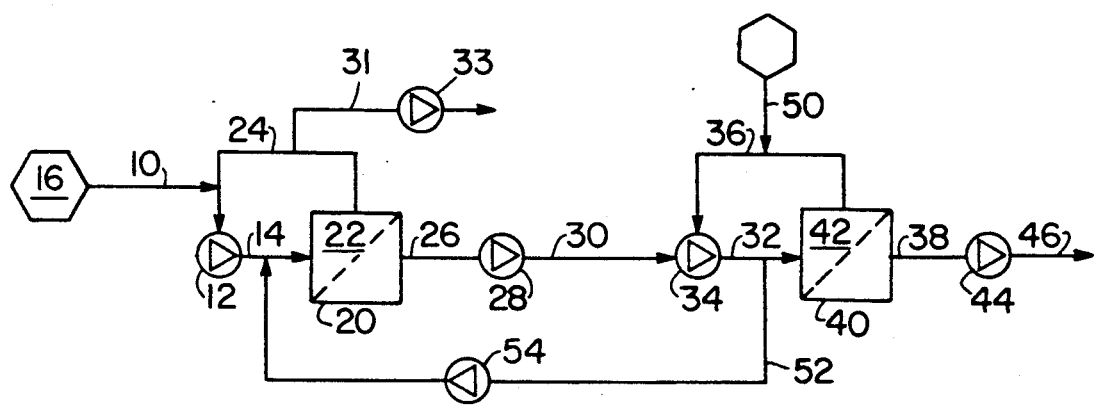
Figure 2E:
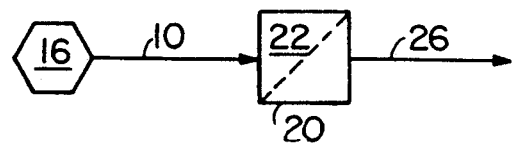

The composite membrane of this invention comprises an asymmetric skinned membrane which functions as an ultrafiltration membrane having a unique microstructure. The membrane of this invention is made by a process similar to that disclosed in U.S. Pat. No. 4,824,568 which is incorporated herein by reference but with additional requirements. Most importantly, the step of coating the porous substrate with polymer solution is effected under carefully controlled conditions onto a microporous substrate to form a skin and an intermediate zone between the exposed skin and the substrate which is porous and is free of voids which extend from the skin t the substrate. Secondly, the compositions of the immersion liquid that controls the removal of polymer solvent and coagulation of the polymer is an organic bath designed to lengthen the polymer coagulation time. In addition, the method of coating the polymer solution onto the porous substrate must be carefully controlled to apply the desired polymer solution thickness uniformly without damaging the substrate and without disrupting the coating so that it remains uniformly thick. The proper combination of intermediate zone thickness and immersion bath composition leads to the desired microstructure and the performance combination of virus particle retention and protein passage in the case of protein solutions containing virus.

The substrate component of the composite membrane is formed of a synthetic material having a substantially continuous matrix structure containing pores or channels of a mean pore size between about 0.05 and 10 micrometers. The substrate can be a microporous membrane, a nonwoven substrate, a woven substrate, or a porous ceramic. A wide variety of polymeric materials can be utilized as the membrane, woven substrate or nonwoven substrate. Examples of these polymers include: polyolefins such as low density polyethylene, high density polyethylene, and polypropylene; vinyl polymers such as polyvinyl chloride and polystyrene; acrylic polymers such as polymethylmethacrylate; oxide polymers such as polyphenylene oxide; fluoropolymers, such as polytetrafluoroethylene and polyvinylidene difluoride; and condensation polymers such as polyethylene terephthalate, nylons, polycarbonates and polysulfones.

The skin and intermediate zones of the composite membrane are made from a polymer solution as described herein. Exemplary polymer solutions can be produced from all of the polymer suitable for forming the porous substrate as set forth above and including solutions of polyvinylidene difluoride, cellulose esters such as cellulose acetate, polyimides such as polyethermide, polysulfones, such as polyethersulfone and polysulfone, polyacrylonitrile and the like.

In one embodiment, the pore surfaces of the porous substrate are treated with a liquid protecting agent to minimize or prevent the polymer solvent employed in subsequent coating steps from attacking these surfaces and from penetrating into the membrane. In the case of microporous membranes formed from polyvinylidene difluoride (PVDF), such as Durapore ® membranes marketed by Millipore Corporation, Bedford, Mass., it has been found that treatment with glycerine is suitable. The membrane can run as a web over a rotating coating roll having its lower portion immersed in a solution of glycerine or can be totally immersed in a glycerine solution.

Liquid protecting agents other than glycerine can be employed including glycols such as ethylene glycol, propylene glycol, triethylene glycol, or the like. Usually, it is preferable to select an agent which is miscible with water because this facilitates removal of the agent in a water bath often used in substrate fabrication to extract from the substrate solvents and other materials employed in forming the substrate. Those skilled in the art will know, or be able to ascertain using routine experimentation, additional liquid protecting agents. The liquid agents can be dissolved in solutions, such as alcohol solutions. This facilitates application of the agent and the alcohol can be removed by subsequent drying.

In general, an amount of agent is employed which is sufficient to provide the preformed substrate with significant protection against attack from the polymer solvents employed in forming the composite membrane having ultrafiltration separation properties and to provide significant protection against substrate penetration by such solvents. The higher concentration of agent is determined by practical considerations. For example, it has been observed that too much glycerine can result in lower adhesion of the ultrafiltration membrane subsequently formed. Cost of the agent is another practical consideration. In treating Durapore ® membranes with glycerine, it has been determined that a preferred treating solution comprises from about 15% to about 40%, by weight, of glycerine in isopropanol. Treating agents that are not liquids can also be employed. For example, water soluble waxes, such as polyethylene oxides, can be melted and applied to the microporous membrane and removed, if desired, subsequently in the processing with a warm water bath.

The treated substrate is dried to remove any carrier for the protecting agent, e.g., isopropanol. Drying can be accomplished by conveying the treated membrane over heated rolls, passing it through a heated convection oven, or by other techniques.

A composite membrane having ultrafiltration separation properties is then formed upon the treated substrate structure. This is effected by coating a polymer solution onto the treated substrate and quickly immersing the coated substrate into a liquid which is miscible with the solvent but is a non-solvent for the polymer. A particularly preferred polymer for the ultrafiltration membrane is PVDF, particularly when the miCroporous substrate is formed from PVDF. Although usually desirable, it is not necessary to form the ultrafiltration membrane from the same polymer forming the substrate. However, in the preferred formation of the composite membrane, the polymer forming the ultrafiltration membrane is the same as the polymer forming the microporous substrate.

Polymer solutions containing between about 10 and 21%, preferably between about 19 and 21% of PVDF in a solvent are employed in order to obtain a ultrafiltration skin of appropriate cut-off. Lower PVDF concentrations lead to more open structures with slightly higher protein passage and lower virus retention. The most selective and retentive structure is achieved using the 19 to 21% preferred PVDF concentration.

In the case of PVDF, the coating process is specifically designed to uniformly deposit a layer of this polymer solution such that the final dry thickness of the coating is between about 5 and 20 microns, preferably between about 5 and 10 microns. Typical knife over roll coating methods, such as generally used to coat ultrafiltration (UF) casting solutions onto substrates, are not optimum for such thin coatings requiring precise thickness control. The knife edge must be set close to the moving substrate to obtain coatings within this narrow range. Such fine settings and adjustments are difficult to obtain due to frictional resistance and the normal tolerance of the knife design. The thickness variability of the substrate being transported under the knife is on the order of the gap (i.e., the space between the fixed knife position and the substrate) that is to be maintained. This variability changes the actual gap and thereby the coating thickness. Also, in the case of a microporous membrane substrate thickness variability can cause breakage when the microporous membrane substrate catches the knife or the frictional resistance becomes too great. The problem is worse for edge curling or scalloping; "floppy edges". When breakage does occur, the knife must be removed, cleaned and reset before continuing. Since breakage of the relatively weak — compared to normal nonwoven substrates — microporous membrane substrate is common, efficiency is reduced.

In order to provide controlled reproducible ultrafiltration skin, a new coating method is provided in accordance with this invention. As shown in FIG. 1, coating thickness is controlled by forming a nip between a rotating drum 76 and a non-rotating rubber coated cylinder 72. The microporous substrate 74 is positioned on a support web 78 which contacts the backed drum or roll 76 which can be rotating. Interposed between the rubber coated cylinder 72 and the polymer solution 84 is a plastic film 82 secured to so as to wrap cylinder 72. This film 82 can be polyethylene terephthalate or any other film that is not adversely affected by the polymer casting solvent and is strong enough to withstand the shear forces imposed on it. The plastic film 82 can extend several inches past the nip point 80 in the direction of web transport and functions as a smoothing film. That is, the film 82 function to smooth the exposed surface of the cast polymer solution 83 which exposed surface forms the skin in the final composite membrane of this invention. It has been found that the use of the cylinder 72 and film 82 permits accurate control of the thickness of the cast film 83 which results in the elimination of undesirable voids in the intermediate zone of the composite membrane.

In operation, casting solution 84 is fed to a reservoir on the web entry side of the nip point 80 of the rubber covered cylinder 72 and the drum 76. The moving microporous substrate 74 drags solution under the nip 80 analogous to journal bearing lubrication. A simplified analysis shows that the coating thickness is proportional to the square root of web speed, casting solution viscosity and length under the nip 80, i.e. the "footprint" of the rubber covered roll; and inversely proportional to the square root of the pressure under the nip. The footprint is controlled by rubber hardness and the pressure forcing the cylinder 72 against the drum.

In practice, solution viscosity and casting speed are set by membrane property requirements. The hardness of rubber coating 85 is chosen empirically to give the desired range of coating thickness. Pressure on the cylinder 72 is then used to set and control the exact thickness observed Pressure is set by pneumatic cylinders 86 acting on the metal core 87 of cylinder 72. By controlling the pressure to the pneumatic cylinders 86, the force on the core 87 is controlled. Coating thickness can then be varied by adjusting the inlet pressure to the pneumatic cylinders 86.

After the polymer solution has been precisely coated onto the microporous substrate, the ultrafiltration membrane structure is formed by immersing the coated microporous substrate into a liquid which is miscible with the polymer solvent but is a non-solvent for the dissolved polymer. A solution comprising 25 wt % glycerine dissolved in water is the preferred liquid for composite membranes made from PVDF at the preferred 19-21% solids concentrate, for example. Although other liquids such as monohydric alcohols, water, or mixtures thereof, can be used, optimal membrane properties are obtained when an organic containing water bath is employed and preferably 25 wt % glycerine in water.

When the precipitation process occurs slowly such as greater than 0.5 minutes, preferably about 0.65 to 1 minute, as is achieved with 25 wt % glycerine in water in a thin coating, a unique asymmetric morphology is obtained in the composite membrane. The composite membrane comprises a skin with ultrafiltration separation properties, a microporous substrate and, in the case of PVDF, an intermediate zone between the skin and the substrate having a thickness between about 5 and 20 microns. The morphology of the intermediate zone is characterized as a continuous matrix structure usually associated with asymmetric microporous membranes but of mean pore size that is substantially smaller and into the ultrafiltration range.

Figure 13:
FIG. 13 is a photomicrograph of a cross-sectional view of a typical membrane produced by the process of U.S. Pat. No. 4,824,568.
Figure 14:
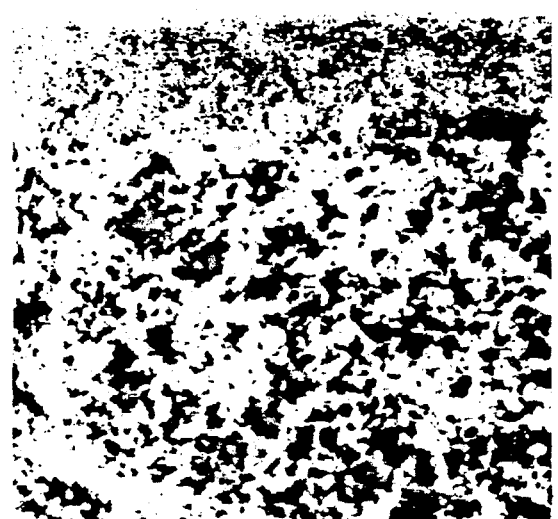
FIG. 14 is a photomicrograph of a cross-sectional view of the membrane produced by the process of this invention.
Figure 15:
FIG. 15 is a photomicrograph of an alternative composite membrane of this invention.

Unlike conventional ultrafiltration membranes as well as those described in U.S. Pat. No. 4,824,568, the structure of the coating on the microporous substrate of this invention is characterized by the absence of elongated voids extending through the intermediate zone from the exposed surface of the skin to the microporous substrate below the intermediate zone. This attribute permits the membrane described herein to be useful in the retention of virus particles while maintaining the protein passage properties characteristic of conventional ultrafiltration membranes. Structures containing infrequent small voids also can result from the process described herein especially at the lower solids content. However, these structures are satisfactory provided that the small voids are infrequent and appear below while not extending to the exposed surface of the skin. However, the preferred structure is one that is a continuous matrix with voids absent. This type of structure is found at the preferred conditions described herein and is shown FIG. 14. This structure is in contrast to the structure of the membrane disclosed in U.S. Pat. No. 4,824,568 as shown in FIG. 13. As shown in FIG. 15, the intermediate zone can contain infrequent larger voids. However these larger voids do not extend from the skin to the substrate as is true with the ultrafiltration membrane shown in FIG. 13.

After the membrane structure has formed, the composite web is prewashed by conveying the coated and precipitated web through a water bath. Contact time of approximately one minute in 25° C. water is sufficient. Drying can be performed by leaving the prewashed web to dry as single sheets at room temperature. Alternatively, the web can be continuously dried by conveying the web over a perforated roll. The interior of the roll is kept at subatmospheric pressure and a heated air stream (e.g., 140° F.) is impinged on the surface of the web. A typical speed for the web over such a roll is 4 to 6 feet per minute.

It has been found that with PVDF polymers and 25 wt % glycerine-water immersion bath that an ultrafiltration membrane less than 5 microns thick is less satisfactory because inadequate surface coverage of the microporous substrate results and the virus retentive properties deteriorate. In some cases a thin coating of less than 5 microns also forms a non-porous collapsed film rather than an open porous structure. When the thickness of the intermediate zone is greater than about 20 microns, undesirable voids can appear in the intermediate zone which can promote virus particle passage. With casting polymer solutions, the minimum and maximum acceptable thickness for the intermediate zone will vary slightly from the 5 to 20 micron range for PVDF. In any event, the intermediate zone is uniformly porous and is free of large voids which extend from the skin to the substrate, unlike the voids found in conventional ultrafiltration membrane.

When the composite membrane of this invention has a skin surface which is hydrophobic, it must be rendered hydrophilic in order to be useful in treating aqueous solutions such as aqueous protein solutions to selectively remove virus particles therefrom. A preferred process for rendering the membrane hydrophilic and low protein binding is disclosed in U.S. Pat. No. 4,618,533 which is incorporated herein by reference. Hydrophilization can be conducted by the process of U.S. Pat. No. 4,618,533 as a continuous multistep process which transforms the hydrophobic membrane into a hydrophilic (water wettable) membrane. In that process, a roll of phobic membrane can be unwound and fed through the following sequence of process steps:

1. Alcohol wetting — The membrane web is submerged or otherwise saturated with an alcohol, typically isopropanol, to completely wet out and fill the porous structure.
2. Water exchange: The membrane web is submerged in a bath of water to replace the alcohol.
3. Saturation with reaction solution: The water wet web is submerged in an aqueous bath of monomer and other reactants made up to the desired composition. Exchange occurs in this bath and the web emerges filled with an aqueous solution containing the reactants. As taught by U.S. Pat. No. 4,618,533, a composition comprising hydroxypropyl acrylate, a crosslinking agent and a suitable initiator, can be used.
4. Polymerization: the web is conveyed to and through a reaction chamber where polymerization of the reactants saturating the web takes place in situ.

Oxygen is excluded during the polymerization reaction. This can be done by saturating the reaction chamber with an inert gas, nitrogen for example; or by sandwiching the web between transparent sheets, such as polypropylene.

5. Washing: After reaction, the web is transported through suitable water wash steps such as submersion, spraying, etc.
6. Drying: The membrane is dried prior to winding and package as described above. The preferred drying temperature is 300° F.

The hydrophilization process described in U.S. Pat. No. 4,618,533 is modified herein to be used with the composite membrane of this invention. Any excess hydrophilization solution is removed from the skin surface of the composite membrane so that the composite pore surface is not covered with a layer of hydrophilic coating that bridges the pores. This can be achieved with, a stationary flexible rubber wiper, a nip roll or the like to remove the excess surface liquid from the surfaces of the composite membrane.

The membranes of this invention are uniquely characterized by a log retention value (LRV; the negative logarithm of the sieving coefficient) for virus particles and other, particles that increases systematically and monotonically with the diameter of the particle; in the size range of interest for virus of 10 to 100 nm diameter. Empirically, the LRV increases continuously with the size of the particle projected area (the square of the particle diameter). The absolute LRV can be adjusted by a corresponding adjustment in the membrane protein sieving properties created by manipulating the coating solution solids content, or immersion bath composition and temperature. The composite membranes of this invention having an intermediate zone of higher porosity have a lower molecular weight cut off than the membranes of this invention having an intermediate zone which is less porous. Where one is concerned with removing small sized virus particles from protein solution, satisfactory LRV of at least about 3 is obtained with membranes having a lower porosity intermediate zone. However, the molecular weight cut off is reduced thereby reducing protein recovery. Therefore, the user will choose a composite membrane which gives satisfactory LRV and protein recovery. In any event, the membranes of this invention are capable of producing an LRV for virus of 3 and can extend to as high as about 8 or greater where the virus particle size is between 10 and 100 nm diameter. In addition, the composite membranes of this invention are characterized by a protein molecular weight cut off of between about $5 \times 10^2$ and $5 \times 10^7$ Daltons. In all cases, the empirical relationship with particle projected area is retained. Log reduction values for virus particles (single solutes in solution; in absence of protein) depends upon the virus particle size. Based upon the relationships illustrated in the examples below, with small sized virus such as hepatitis an LRV of greater than about 3 can be obtained and with larger sized virus such as the AIDS virus, a LRV of greater than 6 can be obtained.

Protein sieving properties can be adjusted to achieve performance typical of conventional ultrafiltration membranes. These properties can be adjusted through proper manipulation of the casting solution solids content and immersion bath composition and temperature as is customary in the formation of ultrafiltration membranes. Higher temperatures promote the formation of larger pores. Higher solids content promote the formation of smaller pores. The membranes of this invention can be formed with molecular weight cut-off values (the molecular weight of the solute that is 90% rejected by the membrane under low polarization conditions) of between $5\times10^2$ Daltons to $5\times10^6$ Daltons.

The composite membrane of this invention can be in the form of a flat sheet or hollow fiber. In the case of a flat sheet, one surface of the substrate, is coated with the skin and intermediate zone. In the case of hollow fiber, the inner or outer surface is coated with the skin and intermediate zone.

In one aspect of this invention, a process is provided for selectively separating viral particles in an apparatus provided with channels or a plurality of hollow fibers wherein the feed stream is flowed tangentially across the skin. A similar device for separating blood plasma into a high molecular weight plasma fraction and a low molecular weight fraction is disclosed in U.S. Pat. No. 4,789,482 which is incorporated herein by reference. In accordance with this invention, a device is provided having a plurality of channels or hollow fibers and which is operated with a controlled flow rate ratio for a recirculation stream to a filter stream.

Referring to FIG. 2*a*, the protein solution contained in vessel 16 which may or may not contain a virus is introduced through conduit 10 by means of a pump 12, passed through conduit 14 and directed to a filtration step 20 wherein protein solution is separated from virus by means of the membrane of this invention 22. The virus rich fraction which also includes protein is recycled to vessel 16 by means of conduit 24. The protein rich fraction free of virus is recovered through conduit 26 by means of pump 28 and is directed to storage or to a point of use through conduit 30.

Other process configurations are possible including the incorporation of a diafiltration stream. Referring to FIG. 2*b*, diafiltration can be added to the process depicted in FIG. 2*a* by introducing to vessel 16 a stream of buffer stored in reservoir 6 through conduit 2 by means of pump 4 operated at a volumetric flowrate that is identical to that of pump 28.

In a second process configuration, a second membrane stage comprised of a module 40 containing the membrane 42 of this invention, can be operated in series with that described above to achieve higher overall virus removal. Referring to FIG. 2*c*, the protein rich fraction of stream 30 created from the process depicted in FIG. 2*a* is added to this second stage. A recirculation stream 36 is introduced to the membrane module 40 containing the membrane 42 of this invention by means of pump 34 and conduit 32. A virus enriched stream is recycled to pump 34 via conduit 36. The protein rich stream from the first stage is introduced via conduit 30 to the recirculation loop created by conduits 32 and 36 and pump 34. Protein rich fraction from the second stage free of virus is recovered through conduit 38 by means of pump 44 and is directed to storage or point of use through conduit 46. The volumetric flowrate through pump 44 is equal to that through pump 28 and pump 12. If desired pumps 28 and 44 can be replaced with throttle valves adjusted to achieve flowrates identical to that of pump 12 and each other.

In another embodiment, a multiple stage cascade an be used which is described herein with reference to FIG. 2*d*. The protein solution contained in vessel 16 which may or may not contain a virus is introduced through conduit 10 by means of pump 12 and passed through conduit 14 and directed to a filtration step 20 wherein protein solution is separated from virus by means of the membrane 22 of this invention. The virus rich fraction which also includes protein is recycled to pump 12 by means of conduit 24. The protein rich fraction free of virus is recovered through conduit 26 by means of pump 28 and is directed to the second filtration stage 40. A virus rich bleed stream 31 is provided from the recirculation loop comprised of conduits 14 and 24 and pump 12 and is withdrawn via conduit 31 and pump 33. A second recirculation stream 36 is introduced to the membrane module 40 containing the membrane of this invention 42, by means of pump 34 and conduit 32. Virus enriched solution from module 40 is recycled to pump 34 via conduit 36. The protein rich stream from filtration module 20 is introduced via conduit 30 to the recirculation loop created by conduits 32 and 36 and pump 34. Protein rich fraction from filtration module 40 free of virus is recovered through conduit 38 by means of pump 44 and is directed to storage or point of use through conduit 46. Optionally, buffer can be introduced to conduit 36 via conduit 50 to maintain constant volume in the cascade. Additionally, to improve protein recovery, part of the fluid contained in the second recirculation loop can be recycled to the first recirculation loop and conduit 14 through conduit 52 by pump 54. In this configuration, the volumetric flowrates in streams 31, 50 and 52 are identical and that of streams 10, 26 and 46 are also identical. The amount of protein recovered and virus removed can be optimized by controlling the ratio of the flowrate of stream 31 to that of stream 46. It is to be understood that a plurality of filtration steps 20 can be utilized in series with appropriate feed and product conduits as shown whereby virus rich stream 24 or 31 can be contacted in additional filtration steps 20 to produce additional protein rich fractions free of virus. These filtration steps can be operated with or without recycle streams. In another embodiment, a dead ended process configuration can be used which is shown herein with reference to FIG. 2*e*, wherein feed is introduced into filtration step 20 and filtrate is removed through conduit 26.

Referring to FIGS. 9 and 10, a typical structure utilizing rectangular hollow channels (FIG. 11) is shown and which can be utilized as seperation module in this invention. This general structure is disclosed in U.S. Pat. No. 4,540,492 which is incorporated herein by reference.

A filter unit 32 comprises, a first membrane 34, a second membrane 36, a first spacer 38, and a second spacer 40 which, when joined together form a plurality of rectangular channels 48. The apparatus utilized for virus separation can include a plurality of filter units 32 which are positioned contiguous to each other and form a stack of filter units 32. Both the first membrane 34 and the second membrane 36 are of identical construction and are formed from the composite membrane of this invention described above. Each membrane 34 and 36 is provided with two longitudinal channels 42 and 44 and a widthwise channel 46. The widthwise channel 46 is not in fluid communication with either of the channels 42 or 44. The first spacer 38 comprises of plurality of channels 48 which extend from edge 50 to edge 52 and outlet channel 54. When membranes 34 and 36 are contiguous to spacer 38, the edges 50 and 52 coincide with the edges 56 and 58 respectively of membrane 36. The second spacer 40 is provided with a protein solution inlet channel 60 and virus-rich stream outlets 62 and 64. The second spacer 40 also is provided with interior channel 68 which provide fluid communication with channels 66, which in turn is in fluid communication with virus-rich stream outlet 64. When spacer 40 is juxtaposed to membrane 36, edges 63 and 65 coincide respectively with edges 56 and 58 of spacer 36. The spacer strips 69 between channels 48 and spacer strips 71 between the channels 66 are bonded to the next adjacent membrane (not shown) and provide the necessary support for the membranes adjacent the channels so that membrane flexibility is controlled to maintain the desired channel height.

While the module structure shown in FIGS. 9 and 10 is useful in the present invention, it is to be understood that any module utilizing the membranes of this invention can be employed in the present invention so long as the operating conditions are controlled aS set forth below.

Referring to FIG. 10, the channels 48, of first spacer 38 are shown to overlap into channels 42 and 44 of membrane 36. This overlap permits introducing a virus-containing protein solution into channel 42, passage of this solution lengthwise along channels 48 while being in contact with membrane 36 and removal of virus-rich solution from channels 48 through widthwise channel 44.

The modules described above, both thin channel and hollow fibers, can be operated in a tangential flow mode at low volumetric conversions. An optimum module aspect ratio and corresponding optimum operating conditions exist for the separation of virus particles from protein solutions. The optimum aspect ratio and operating conditions are in accordance with those described in U.S. Pat. No. 4,789,482 which is incorporated herein by reference. The aspect ratio, L/h, to achieve high solute recovery is defined by Equation 1:

$$L/h = [K/12 \, \rho\mu - h/L_p]^{\frac{1}{2}} \qquad \text{Equation 1}$$

K is a function of the ratio of the transchannel pressure drop to the average pressure in the channel. K is obtained experimentally by the procedure set forth below. h is the channel height or the hollow fiber radius, $\rho$ is the ratio of the recirculation stream flow rate, $Q_R$, to the permeate stream flow rate, $Q_p$, $\mu$ is the viscosity of the incoming protein stream being separated, L is the length of the channel or fiber and $L_p$ is the membrane hydraulic permeability after the membrane is wet with the liquid to be ultrafiltered.

For channels of rectangular geometry having at least one wall formed of a porous membrane, h is the distance between the membranes 90 and 92 which define the height of the channel shown in FIG. 11. Generally h for the rectangular channels is between about 0.0110 and 0.030 cm. In the present invention, the module aspect ratio, L/h, can range between about 50 and 5000, preferably 200 to 300.

The module aspect ratio and module operating shear rate are simultaneously optimized to achieve the desired selectivity at the largest possible flux. Unlike conventional systems, this system does not operate either at an excessively large shear rate or an excessively low volumetric flux, but at conditions which maximize the desired selectivity which in the case of virus removal is the virus to protein selectivity. An exact relationship has been found between the module aspect ratio and module operating shear rate which gives optimal separation performance.

The maximum shear rate to be utilized in the apparatus is defined by equation 2:

$$\gamma = \frac{p^2 D^* \mu^{1/2}}{L_p^{1/2} h^{3/2}} \frac{1}{(1+K)^2} \qquad \text{Equation 2}$$

wherein $\delta$ is the maximum shear rate to obtain optimal selectivity performance.

The proportionality constant, $D^*$, is obtained empirically by the following procedure:

A prototype module is provided containing a plurality of thin channels or hollow fibers of the type of ultrafiltration membrane to be utilized in the final apparatus. The channels or fibers in the prototype can be of any dimension. A prototype having channels with an L/h of about 200 has been found to be useful. Pumps and conduits are provided to form a flux stream to recover the low molecular weight component and to control the flow rate of the permeate, $Q_p$. This permeate stream is recombined in a feed reservoir with a recirculation stream comprising the high molecular weight component obtained from the ultrafiltration channels or fibers. The recirculation stream flow rate ($Q_R$) is controlled. A plurality of runs are made with the apparatus with either $Q_p$ being varied and $Q_R$ being maintained constant or $Q_R$ being varied and $Q_p$ being maintained constant. After each run, the separation performed (selectivity) between the species of interest is measured. After each run the system also is thoroughly flushed such as with saline or water to remove all treated liquid from the system. A standard hydraulic permeability, e.g. water or saline, $L_p$, is then measured by standard methods. The value then is multiplied by the ratio of $\mu$ of the treated liquid to $\mu$ of the standard fluid wherein $\mu$ is viscosity in centipoises and wherein $L_p$ is used in equation 1. From the selectivity values obtained, the optimum selectivity is identified and the $Q_p$ and $Q_R$ values which correspond to the optimum selectivity can be determined. The selected optimum value refers to the $Q_p$ and $Q_R$ values when both the flux and selectivity are maximized simultaneously. The constant K can be calculated using the optimum value of $Q_R/Q_p$ using Equation 1.

Using the shear rate corresponding to the optimum $Q_R$, the constant $D^*$ then can be calculated from equation 2. $D^*$ is a property of the solution being ultrafiltered and for proteins is between about $1\times10^{-7}$ cm²/sec and $25\times10^{-7}$ cm²/sec. The limits on $\rho$ reflect the limits on the ratio, $Q_R/Q_p$. The upper limit is set by the size of the recirculation pump whereas the lower limit is set by the virus retention which decreases at low values of $Q_R/Q_p$, i.e. at high conversions, (the retained species become more concentrated as permeate is removed). For small viruses, the value of $Q_R/Q_p$ greater than 20 to 1 are preferred.

When an ultrafiltration device is designed and operated in accordance with equations 1 and 2, the total membrane area in the device which provides optimal separation efficiency is give by equation 3:

$$A=0.25\, Q_p L(1+K)^2/D^*K\,(\mu L_p/h)^{\frac{1}{2}} \qquad \text{Equation 3}$$

wherein A is the total membrane surface area.

Furthermore, the maximum transchannel pressure drop which can be measured directly is also given by equation 4 for optimal separation conditions:

$$P_C=2.0 D^* h^{\frac{1}{2}}/(1+K)^2\, L_p^{3/2}\, L\mu^{\frac{1}{2}} \qquad \text{Equation 4}$$

wherein $\Delta PC$ is the transchannel pressure drop.

Control of the concentration polarization in a tangential flow module depends both upon a combined match between the module aspect ratio and operating shear rate Therefore, only a restricted range of module designs and of operating shear rate are feasible. This results in an upper and lower limit for the factors, L/h, and $\rho$. The ratio $\rho$, of recirculation stream flow rate, $Q_R$, to permeate stream flow rate $Q_p$, is between about 5 and 100, preferably between about 10 and 50 and most preferably 30.

Finally, with the optimal design, L/h, and operating conditions, $\delta$, the ratio of the transmembrane pressure drop at the channel outlet to the transmembrane pressure drop at the channel inlet, $$b=TMP_{Outlet}/TMP_{Inlet}$$

is significantly different from 1.0. The value of b derived from this invention lies between 0.0 and 0.85, most typically 0.75.

As is shown in the examples, optimal virus separation and protein recovery is achieved under the conditions shown in U.S. Pat. No. 4,789,482, however, the preferred values of aspect ratio and operating conditions differ from those identified in the claims of that patent. As shown in the examples, in the presence of protein, virus removal (LRV), is a function of both aspect ratio and the ratio of recirculation flowrate, $Q_R$, to permeate flowrate, $Q_p$. The range appropriate to virus retention are shown to be an aspect ratio of between 100 to 1000 and a value for $\rho$ of between 20 and 200. These ranges are within those described in U.S. Pat. No. 4,789,482. However, in the absence of protein, the preferred aspect ratio is about 300 and the preferred value of $\rho$ is between 20 and 100. Aspect ratios of below 100 and above 1000 both result in less virus retention; values of $\rho$ below 20, i.e. conversions above 0.05, can be used, but result in a similar dramatic loss in virus retention.

In the presence of protein, such as human serum albumin, the virus retention is enhanced by protein polarization on the membrane surface. In this case, virus retention is much less affected by aspect ratio and is nearly independent of same as long as the value of $\rho$ is above 10, i.e. as long as the conversion is below 0.1. Therefore, in the presence of protein, the aspect ratio of between 100 to 500 is preferred and a value of $\rho$ of between 10 and 50 is most preferred.

Combining these two cases for general use, the values of aspect ratio and $\rho$ are those described in U.S. Pat. No. 4,789,482, with the preferred aspect ratio of about 300 and the preferred value for $\rho$ of between about 20 and 30.

The following examples illustrate the invention and are not intended to limit the same.

EXAMPLE I

A Durapore ® microporous membrane having an average pore size of 0.22 micrometers and marketed by Millipore Corporation, Bedford, Mass. was employed as the preformed microporous membrane. The membrane was treated with a 30% glycerine in isopropanol solution and dried.

A polymer solution containing 20.5% polyvinylidene difluoride (PVDF, Kynar 741, Pennwalt Corporation, Philadelphia, Pa.) and, 4.9% lithium chloride in N-methyl Pyrrolidone (NMP) was cast onto the glycerinized Durapore ® microporous membrane at a speed of 15 feet per minute utilizing the apparatus illustrated in FIG. 1, the coated membrane was then immersed in a 25 wt % glycerine in water bath maintained at a temperature of 7° C. The length of the polyester smoothing film of the coating process described with reference to FIG. 1 is approx. 2–3 inches. The air exposure between the coating polyester film and immersion bath was 2 inches. After casting, the composite membrane was immersed in a water bath maintained at 25° C. for one minute and was subsequently dried by conveying the prewashed web over a perforated drying roll having subatmosphere pressure and a heated air stream (140° F.) impinging on the surface of the web which was moving at 6 feet per minute.

The general procedure used to render the membrane hydrophilic is that described in U.S. Pat. No. 4,618,533 which is described above. For the membrane used in this example, the reactant aqueous solution contained 4% hydropypropyl acylate (HPA), crosslinking agent and free radical initiator. The hydrophobic membrane was sequentially and continuously conveyed through alcohol, water and reactant both at 25 feet per minute. The excess reaction solution was removed by means of flexible rubber wiper blades. PolymerizatiOn of the crosslinked copolymer was initiated by UV light with a wavelength of 254 nanometers applied to both sides of the web. The reactant saturated web had a residence time of approximately 5–10 seconds in the UV light. The hydropholized web was washed in water to remove excess reactants and dried on a perforated drum, the interior of which was held at subatmospheric pressure, while air heated to 300° F. was imPinged on the surface.

During the coating operation, the rubber roll nip pressure as applied by the pneumatic cylinders and the speed at which the microporous substrate was pulled through the nip were varied in these membranes in order to produce intermediate porous zone thicknesses as measured by SEM from 5 to 20 micrometers. The nip pressure was varied from 85 to 175 psi and the speed from 6.5 to 15 feet per minute.

The membrane B produced was challenged separately and independently with two different solutions, one a solution containing only Phi X 174 bacteriaphage in phosphate buffered saline (PBS) and a second solution containing 0.25% human serum albumin in PBS spiked with Phi X 174 bacteria phage.

Figure 3A:
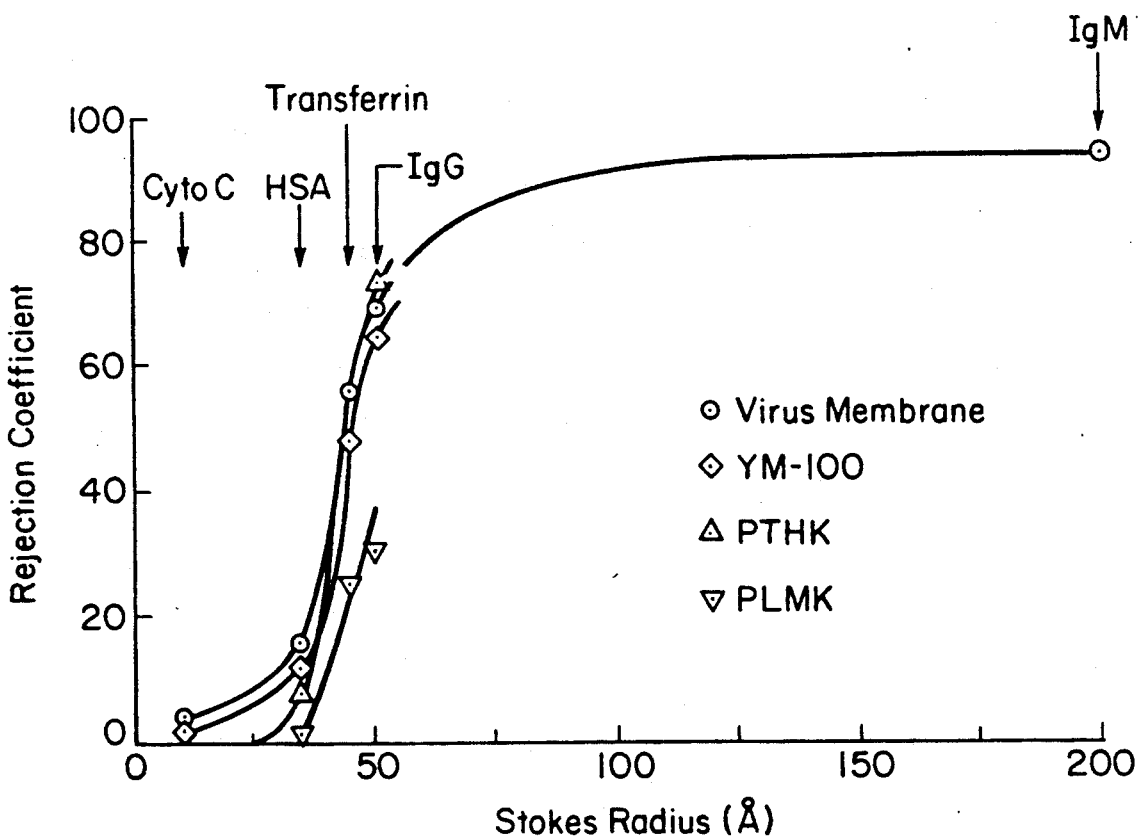
FIG. 3 is a graph of the log reduction value of PhiX174 and the sieving coefficient of human serum albumin as a function of the thickness of the intermediate porous zone.
Figure 3B:
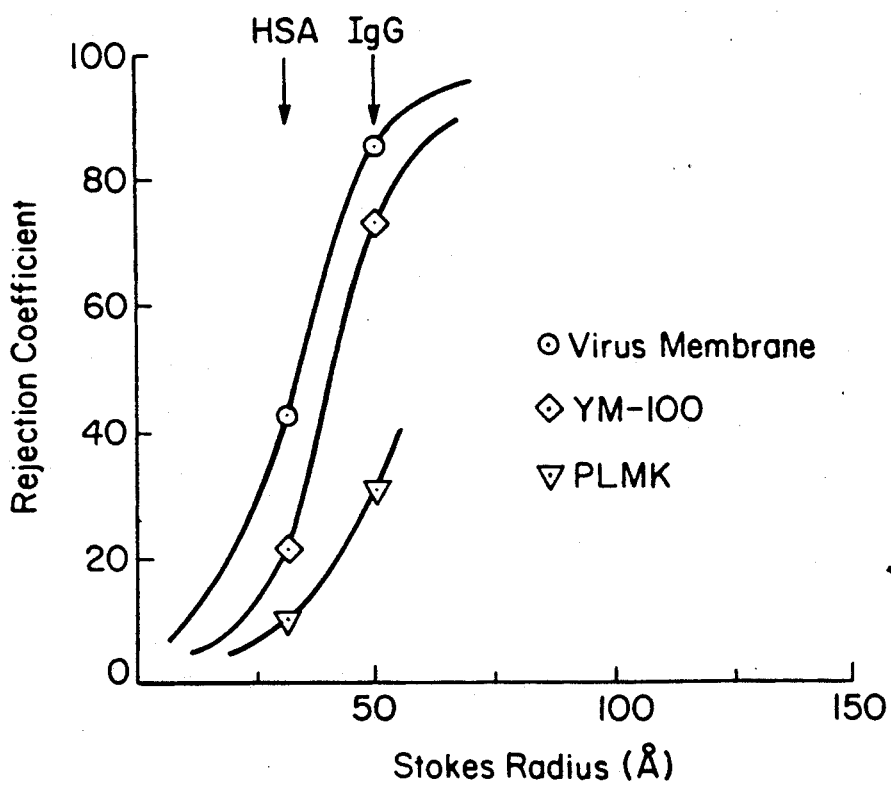

As shown in FIG. 3, at a thickness of the dried hydrophobic intermediate zone of 5 micrometers, the intermediate porous zone is significantly collapsed resulting in low solute permeability, Phi X 174 LRV is very high, about 5 logs, and albumin sieving is very low at 48%. As the thickness of the intermediate zone is increased to 8 micrometers, the zone and the surface skin become more permeable resulting in a significant increase in protein passage and a loss in Phi X LRV. As the intermediate zone thickness is increased further to 20 micrometers, the Phi X LRV decreases at a much lower rate and albumin passage is unchanged.

EXAMPLE II

This example illustrates that the composite membranes of this invention are capable of retaining virus particles in the absence of protein at log reduction values that are significantly better than membranes of the prior art possessing equivalent protein sieving characteristics. Additionally, the particle log reduction valves of membranes of this invention increase monotonically as a function of the particle diameter, a property not observed with membranes of the prior art.

A first membrane of this invention identified as Membrane A was prepared as follows:

A Durapore ® microporous membrane having an average Pore size of 0.22 micrometers and marketed by Millipore Corporation, Bedford, Mass., was employed as the preformed microporous membrane. The membrane was treated with a 30% glycerine in isopropanol solution and dried.

A polymer solution containing 19.8% polyvinylidene difluoride (PVDF, Kynar 741, Pennwalt Corporation, Philadelphia, PA) and, 5% lithium chloride in methyl pyrrolidone was cast onto the glycerninized Durapore ® microporous membrane at a speed of 15 feet per minute utilizing the apparatus illustrated in FIG. 1. the coated membrane was then immersed in a 25 wt % glycerine in water bath maintained at a temperature of 7° C. The length of the polyester smoothing film of the coating process described with reference to FIG. 1 is approx. 2–3 inches and the pressure of the pneumatic cylinders is 150 psi. The air exposure between the coating polyester film and immersion bath was 2 inches. After casting, the composite membrane was immersed in a water bath maintained at 25° C. for 1 minutes and was subsequently dried by conveying the prewashed web over a perforated drying roll having subatmosphere pressure and a heated air stream (140° F.) impinging on the surface of the web which was moving at 6 feet per minute.

Membrane A was hydrophilized as described in Example 1.

The dried hydrophobic composite membrane had an intermediate porous zone thickness of 7.2 to 9.6 microns as determined by a scanning electron microscope (SEM).

A second membrane of this invention identified as Membrane C was prepared as follows:

A Durapore ® microporous membrane having an average pore size of 0.22 micrometers and marketed by Millipore Corporation, Bedford, Mass. was employed as the preformed microporous membrane. The membrane was treated with a 30% glycerine in isopropanol solution and dried.

A polymer solution containing 19.8% polyvinylidene difluoride (PVDF, Kynar 741, Pennwalt Corporation, Philadelphia, Pa.) and, 5% lithium chloride in methyl pyrrolidone was cast onto the glycerninized Durapore ® microporous membrane at a speed of 15 feet per minute utilizing the apparatus illustrated in FIG. 1. The coated membrane was then immersed in a 25 wt % glycerine in water bath maintained at a temperature of 7° C. The length of the polyester smoothing film of the coating process described with reference to FIG. 1 is about 2 inches and the pressure supplied to the pneumatic cylinders is 150 psi. The air exposure between the coating polyester film and immersion bath was 2 inches. After casting, the composite membrane was immersed in a water bath maintained at 25° C. for 1 minutes and was subsequently dried by conveying the prewashed web over a perforated drying roll having subatmosphere pressure and a heated air stream (140° F.) impinging on the surface of the web which was moving at 6 feet per minute.

The composite membrane was rendered hydrophilic by the following procedure:

membrane C was hydrophilized similarly to Membrane A. The impingement drying air temperature was 275° F. The aqueous reactant concentration contained 5.1% hydroxypropyl acrylate, crosslinking agent and free radical initiator.

The dried hydrophobic composite membrane had an intermediate porous zone thickness of 8.5 microns as determined by a scanning electron microscope (SEM).

A third membrane of this invention identified as Membrane D was prepared as follows:

A Durapore ® microporous membrane having an average pore size of 0.22 micrometers and marketed by Millipore Corporation, Bedford, Mass. was employed as the preformed microporous membrane. The membrane was treated with a 30% glycerine in isopropanol solution and dried.

A polymer solution containing 19.9% polyvinylidene difluoride (PVDF, Kynar 741, Pennwalt Corporation, Philadelphia, Pa.) and, 4.9% lithium chloride in methyl pyrrolidone was cast onto the glycerninized Durapore ® microporous membrane at a speed of 15 feet per minute utilizing the apparatus illustrated in FIG. 1. coated membrane was then immersed in a 25 wt % glycerine in water bath maintained at a temperature of 8° C. The length of the polyester smoothing film of the coating process described with reference to FIG. 1 is about 2 inches and the pressure supplied to the pneumatic cylinder is 150 psi. The air exposure between the coating polyester film and immersion bath was 2 inches. After casting, the composite membrane was immersed in a water bath maintained at 25° C. for 1 minute and was subsequently dried by conveying the prewashed web over a perforated drying roll having subatmosphere pressure and a heated air stream (140° F.) impinging on the surface of the web which was moving at 4 to 6 feet per minute.

Membrane D was hydrophilized continuously with membrane A.

The dried hydrophobic membrane had an intermediate porous zone thickness of 8.1–9.3 microns as determined by a scanning electron microscope (SEM).

Membrane A was compared with commercially available ultrafiltration membranes, PTHK, membrane PLMK membrane, both available from Millipore Corporation of Bedford, and YM-100 membrane available from Amicon Corporation, Danvers, Mass. to determine the protein sieving characteristics as a function of protein size and operating flux at a constant recirculation flow rate to achieve a shear of 1100 $1/_{sec}$.

Figure 4:
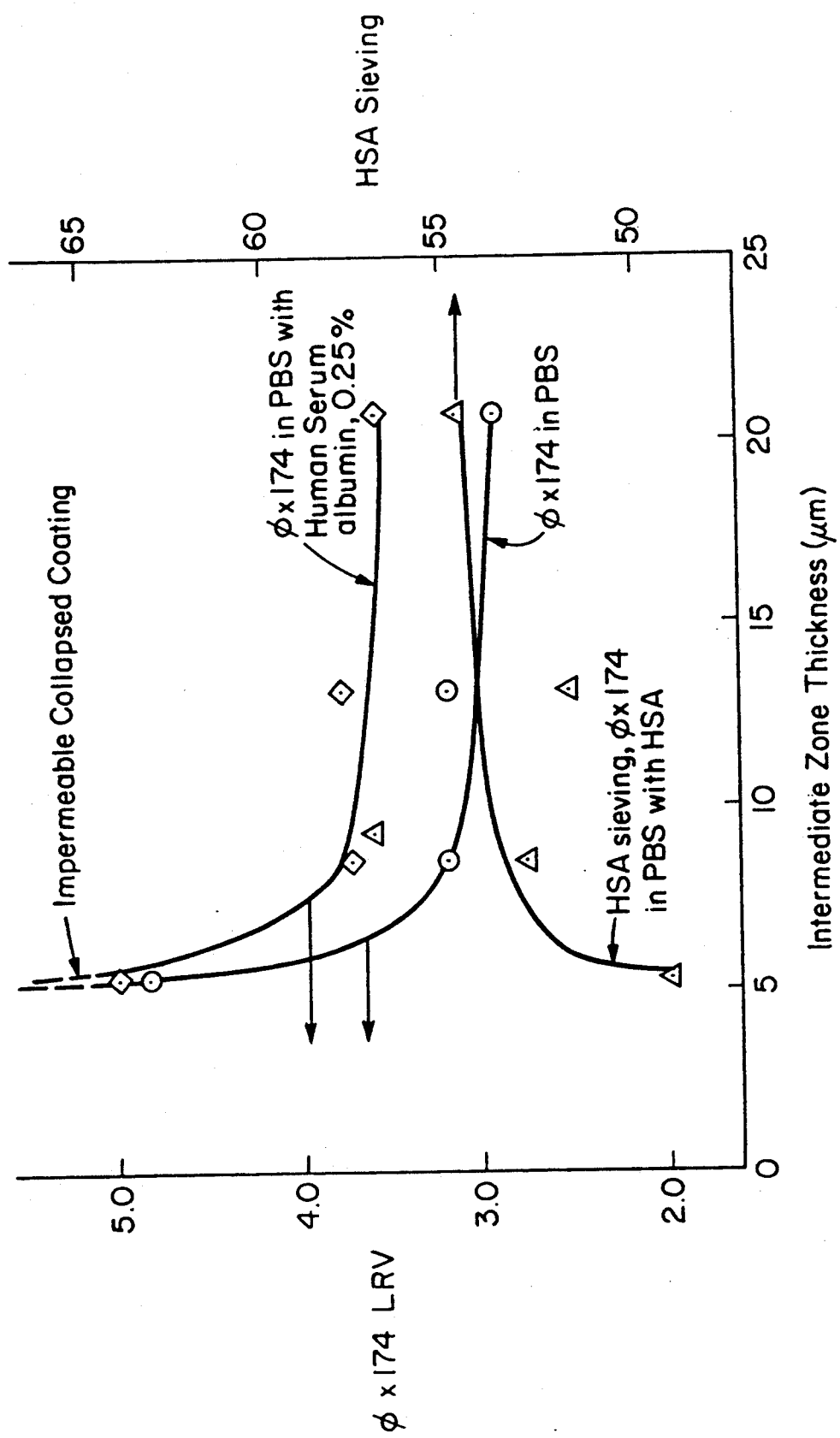
FIG. 4 is a graph of the rejection coefficient of proteins of various size as a function of their Stokes radius for membrane A of this invention and commercially available ultrafiltration membranes.

At both 0.6 liters/meters $^2$/hr (LMH) and 6.0 LMH the protein sieving characteristics of the virus Membrane A is essentially equivalent to that of a typical 100,000 dalton cut-off commercially available ultrafiltration membrane. In both cases, the virus Membrane A is substantially tighter than the Millipore PLMK membrane of 500,000 dalton cut-off as shown in FIG. 4.

The log reduction values of the three membranes of this example set forth above were compared with commercially available YM-100 membrane available from Amicon Corp. of Danvers, Mass.; PTHK membrane available from Millipore Corporation of Bedford, Mass. both shown previously to have nearly identical protein sieving properties. Also included are two membranes identified as PZHK#1 and PZHK#2 made in accordance with Example 2 of U.S. Pat. No. 4,824,568 and hydropholized as described above and the commercially available UltiPor 0.04 micrometer membrane available from Pall Corporation of East Hills, N.Y.

The log reduction value was determined by the following procedure. Each membrane was challanged with a solution containing the challange particle in phosphate buffered saline in a tangential flow cell under conditions of 1100 sec $^{-1}$ shear and a flux of 3 liters per square meter per hour. Samples of filtrate and challange solution were analyzed for particle concentration and the LRV calculated as the logarithm of the ratio of the challange concentration to the filtrate concentration. Two challange particles are bacterial phage, Phi X 174 and Phi 6 and are assayed by a plaque assay using their respective host bacteria. A dilution series was generated to determine concentration. The particles are latex particles available from Seragen Diagnostics, Inc., Indianapolis, Ind. These latex particles were stabilized with 0.1% Triton X-100 surfactant to avoid agglomeration. The latex particles were assayed by first collecting via dead-ended vacuum filtration, 10-50 mls of filtrate onto a 25 millimeter disc of 0.03 micron or 0.05 micron Nucleopore filter available from Nucleopore Corp., Pleasanton, Calif. A representative portion of the Nucleopore filter disc is mounted on an SEM stage and photomicrographs of in excess of 20 fields are recorded. The particles observed in these photomicrographs are counted to determine the concentration of latex in each sample.

Figure 5:
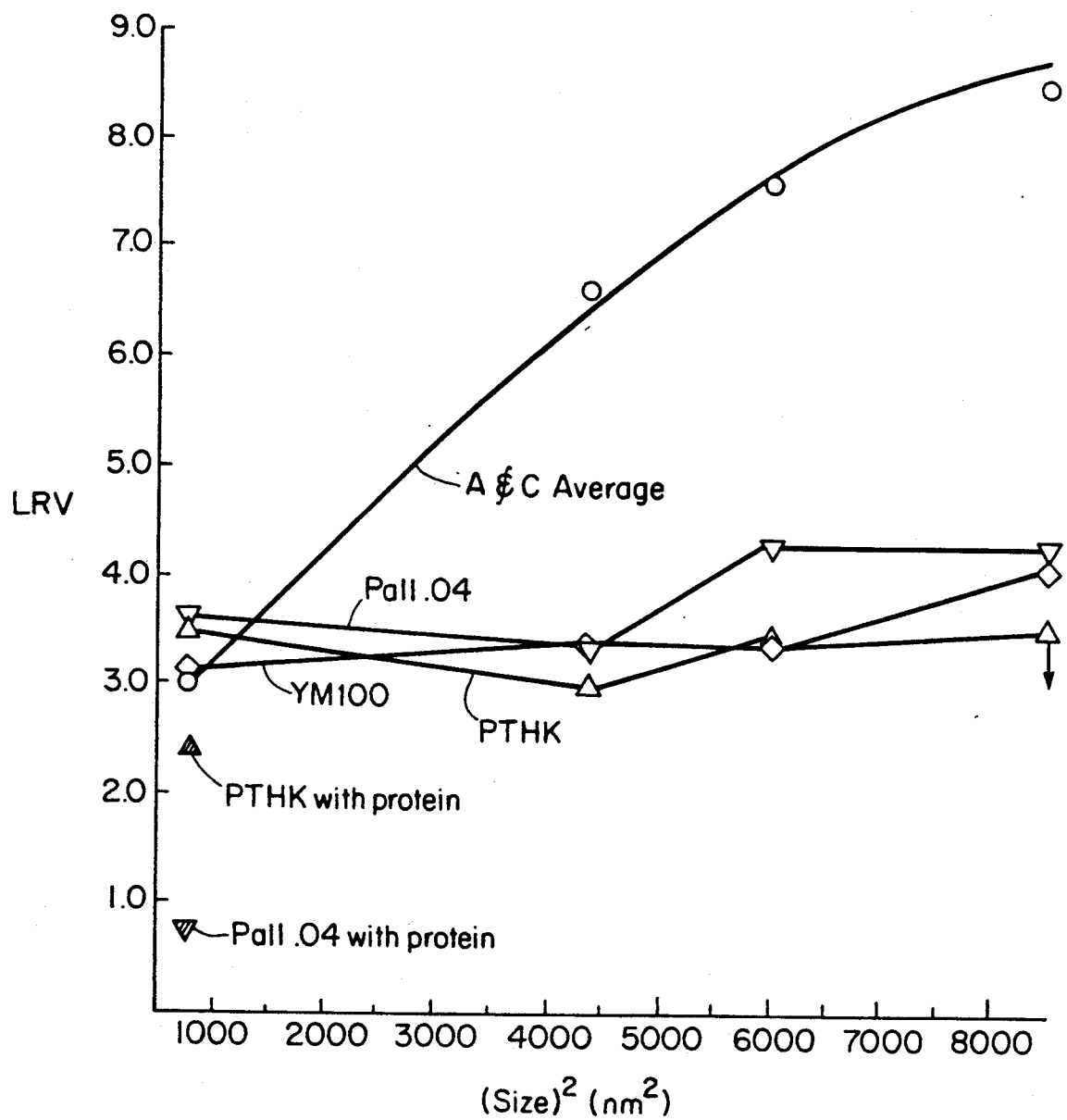
FIG. 5 is a graph of the log reduction values of particles as a function of the square of the particle diameter.

A comparison of the log reduction values of these membranes is shown in FIG. 5 and Table 1.

As shown in FIG. 5 and Table 1, only the membranes of this invention were capable of removing viral-sized particles from solution with a log retention value that increases monotonically as a function of particle diameter up to a value of 8.1 LRV for a 93 nm diameter particle. Commerically available ultrafiltration membranes of similar protein sieving properties show LRV values that are nearly independent of particle diameter increasing only ½-1 log over the size range measured. The membranes of this invention provide at least 3 to 4 orders of magnitude improvement in particle removal for particles above 70 nm diameter as compared to these commercially available ultrafiltration membranes. Additionally, as is shown in Table 1, the performance of the membranes of this invention is very reproducible.

When compared with PZHK#1 and PZHK#2, the improvements in the casting technology described herein over that of U.S. Pat. No. 4,824,568 have led to 3-5 log performance improvement over the entire particle size range measured.

Finally, the PTHK and Ultipore membranes demonstrated a loss in retention of Phi X 174 in the presence of HSA protein as is shown in FIG. 5, suggestive of the fact that Phi X 174 adsorption is contributing significantly to the particle removal measured with these two membranes. In the presence of HSA, the LRV of Phi X 174 is increased from 3.0 logs to 3.7 logs due to protein concentration polarization with the Membrane A and the Membrane C virus membranes of this invention. Therefore, the measured removal of particles is being accomplished primarily on the basis of size.

TABLE I

| PARTICLE LOG REDUCTION VALVES | | | | |
|---|---|---|---|---|
| MEMBRANE | Phi X (28 nm) | 67 nm latex | Phi 6 (78 nm) | 93 nm latex |
| A | 2.9 | 6.5 | >7.5 | 8.2 |
| C | 3.0 | 6.7 | | 8.0 |
| D | 3.1 | | >7.5 | |
| PTHK | 2.2 | <3.06 | 3.5 | <3.5 |
| YM-100 | 3.1 | <3.4 | 3.3 | 3.9 |
| Pall .04 micron | 0.7 | <3.3 | 4.2 | 4.2 |
| PZHK #1 | 0.08 | — | 1.92 | — |
| PZHK #2 | 0.025 | — | 0.14 | — |

EXAMPLE III

The membrane of this invention identified as Membrane A and prepared as described above was tested to determine the effect of tangential flow operation conditions upon the capability to retain Phi X 174 bacterial virus.

The composite membrane was incorporated into an apparatus similar to that shown in FIGS. 9 and 10 which had one module 32 and having channels 2.4 inches long and 0.0078 to 0.0063 inch high.

A 0.25 wt. % Human Serum Albumin protein solution (Alpha Therapeutic) was prepared which included Phi X 174 bacterial phage having a 28 nm diameter at pH 7.4. The solution was passed through the separation apparatus in order to determine LRV as a function of flux through the membrane and as a function of the ratio of the recirculation flow rate to filtrate flow rate. The results are shown in FIGS. 6 and 7.

Figure 6:
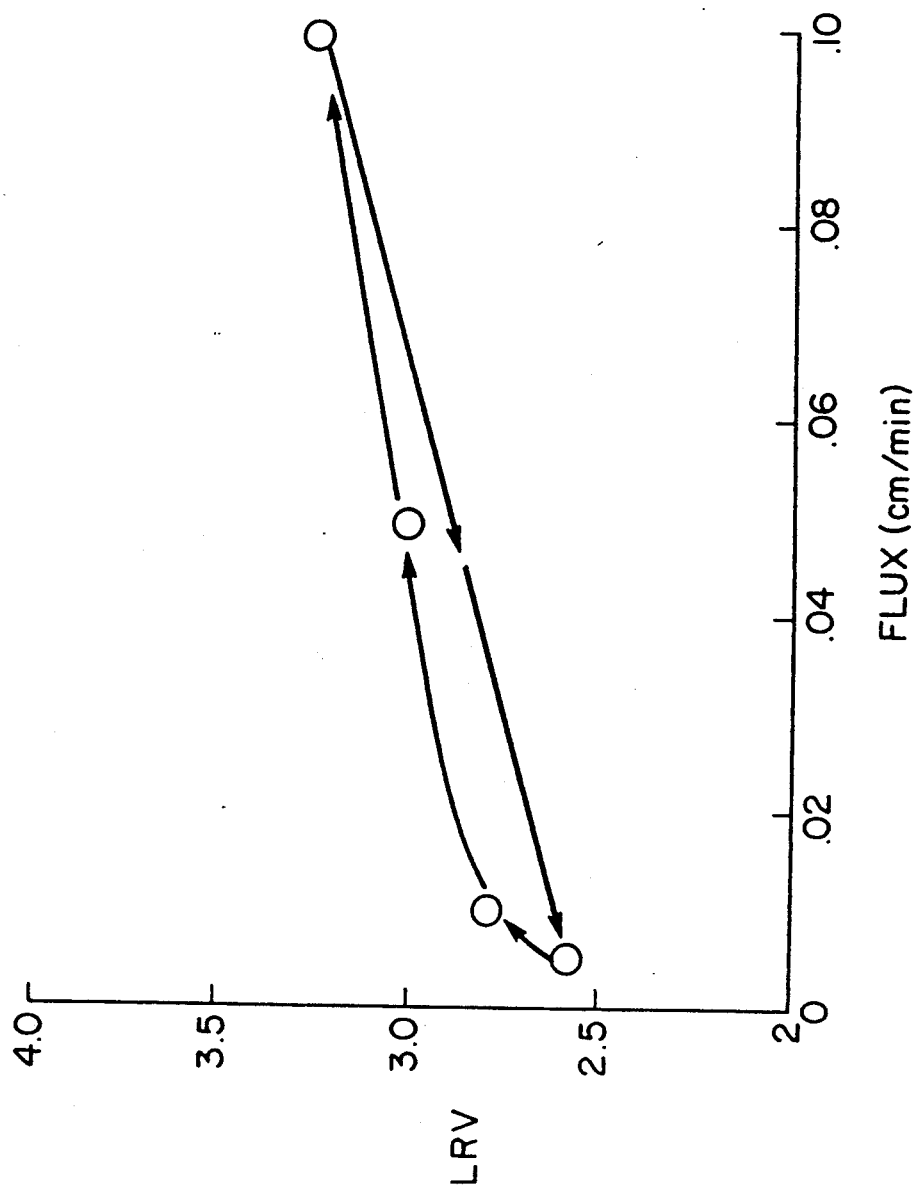
FIG. 6 shows the log reduction value of PhiX174 as a function of volumetric flux of the membrane produced in Example 3.
Figure 7:
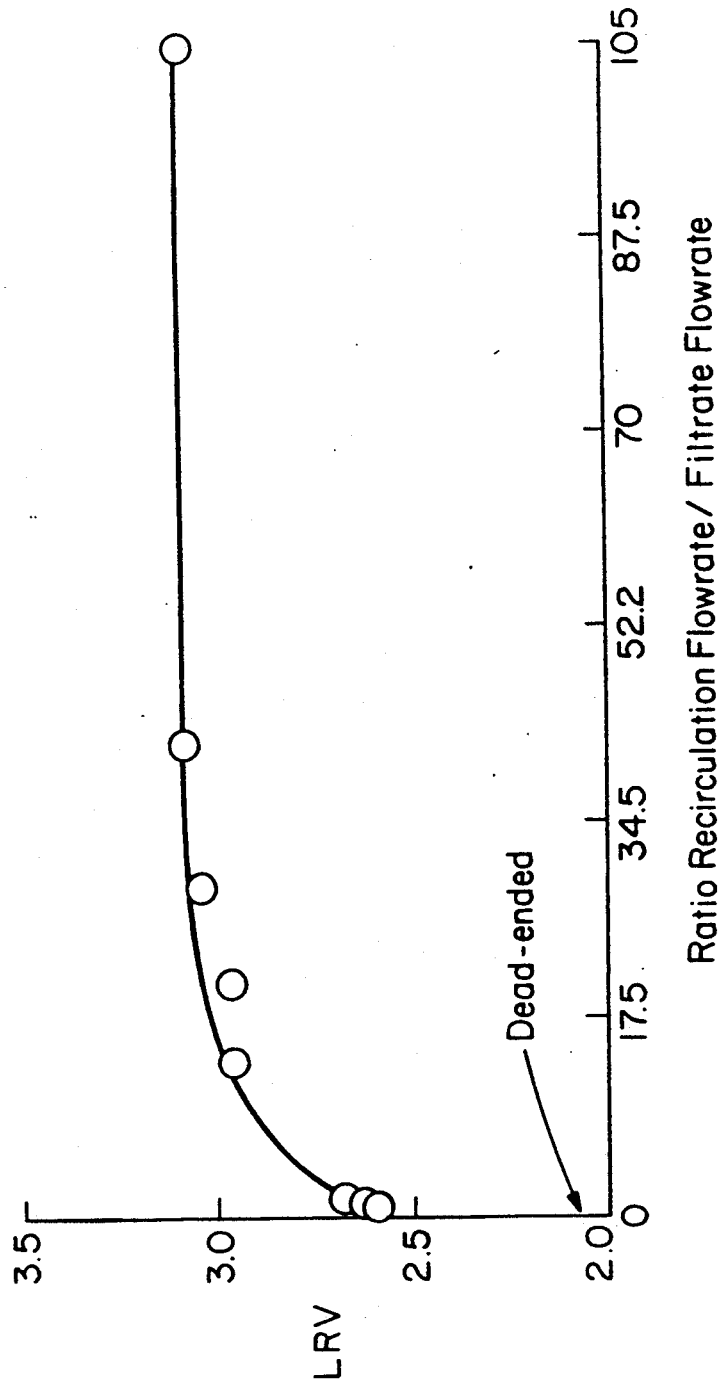
FIG. 7 shows the log reduction value of PhiX174 as a function of the ratio of the recirculation flow rate to filtrate flow rate of the membrane produced in Example 3.
Figure 8:
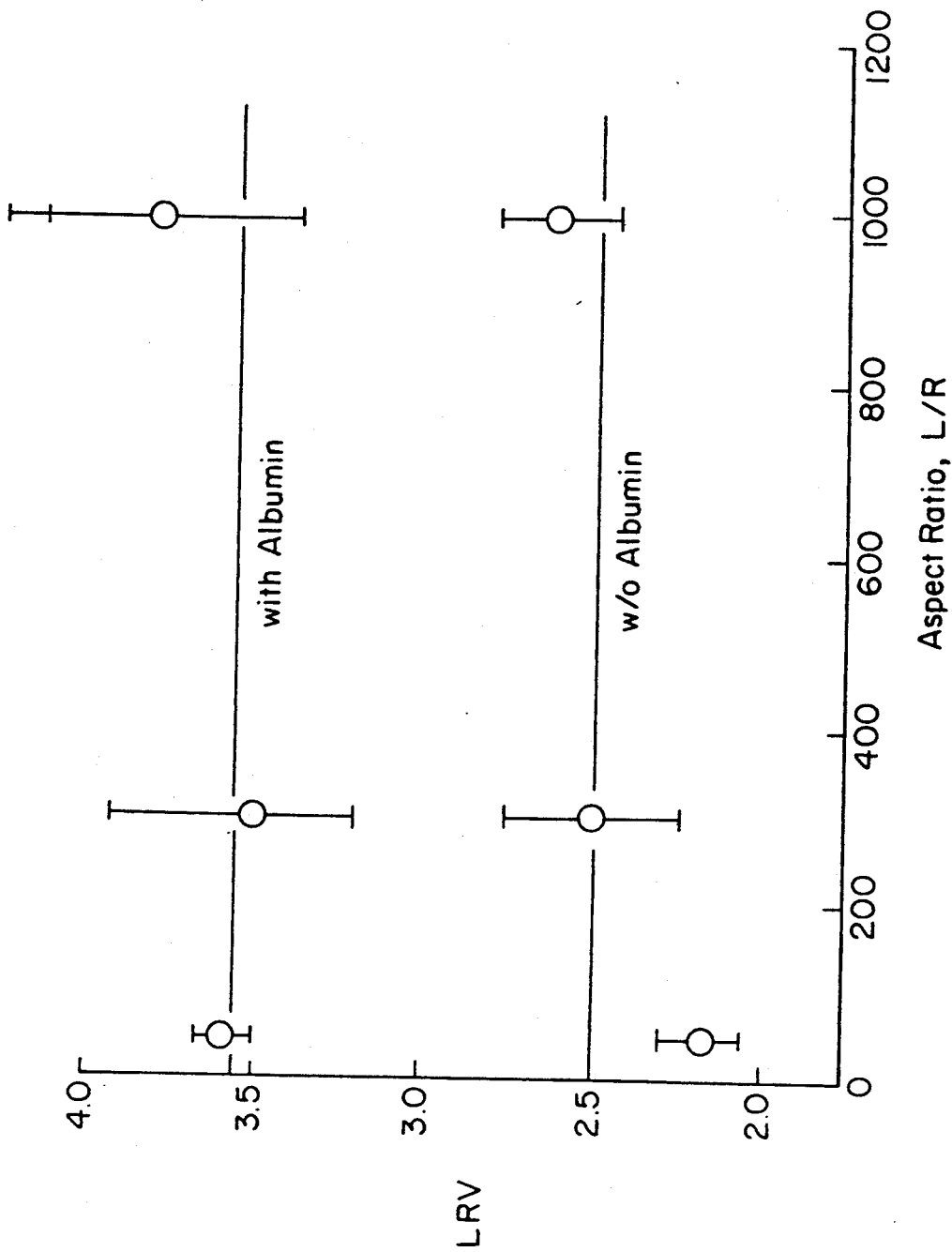
FIG. 8 shows the log reduction value of PhiX174 as a function of the channel aspect ratio.

As shown in FIG. 6, the retention of the phage increases slightly as a function of transmembrane flux but the performance is reversible when the flux is returned to a low value, performance that is consistant with protein concentration polorization.

The PVDF composite membrane of this invention was tested to determine the effect of the ratio of recirculation flow rate to filtrate flow rate on LRV. As shown in FIG. 7, Phi X 174 retention is increased above that a dead end filtration device as the value of this flowrate ratio is increased. Therefore, as either the recirculation flow rate is increased or the conversion (the reciprocal of this flowrate ratio) is decreased, the Phi X 174 retention is improved over that measured in dead ended filtration in which the recirculation flow rate is zero and the conversion is 100%. As can be seen in FIG. 7, the phage LRV is independent of the ratio of recirculation flow rate to filtrate flow rate above a value of 25:1.

EXAMPLE IV

The membrane of this example, Membrane E, was tested in the apparatus similar to those shown in FIGS. 9 and 10 which had one module 32 and having channels 2.4 to 11.0 inches long and 0.004 to 0.030 inches high such that the effect of channel aspect ratio on virus log reduction could be determined.

Membrane E was prepared as follows:

A Durapore® microporous membrane having an average pore size of 0.22 micrometers and marketed by Millipore Corporation, Bedford, Mass. was employed as the preformed microporous membrane. The membrane was treated with a 30% glycerine in isopropanol solution and dried.

A polymer solution containing 20% polyvinylidene difluoride (PVDF, Kynar 741, Pennwalt Corporation, Philadelphia, Pa.) and, 5% lithium chloride in methyl pyrrolidone was cast onto the glycerinized Durapore® microporous membrane at a speed of 15 feet per minute utilizing the apparatus illustrated in FIG. 1. coated membrane was then immersed in a 25 wt % glycerine in water both maintained at a temperature of 7° C. The length of the polyester smoothing film of the coating process described with reference to FIG. 1 is approx. 2–3 inches and the pressure supplied to the pneumatic cylinder is 150 psi. The air exposure between the coating polyester film and immersion bath was 2 inches. After casting, the composite membrane was immersed in a water bath maintained at 25° C. for 1 minute and was subsequently dried by conveying the prewashed web over a perforated drying roll having subatmosphere pressure and a heated air stream (140° F.) impinging on the surface of the web which was moving at 4 to 6 feet per minute.

Membrane E was hydrophilized as described in Example 1.

The dried hydrophobic membrane had an intermediate porous zone thickness of 6–10 microns as determined by a scanning electron microscope (SEM).

The results when challanged with a PBS solution containing Phi X 174 both in the presence and absence of HSA are shown in FIG. 8. All tests were conducted at a channel shear rate of 1100 $sec^{-1}$ and at a 3 liter per square meter per hour flux. The channel aspect ratio has little effect on the retention of virus above a value of about 100.

EXAMPLE V

The membrane of this invention, identified as Membrane A and prepared as described above, was used in the two stage system of FIG. **2*d*** to demonstrate the performance in a system as could be employed in practice. The two stage system was operated under tangential flow conditions at a recirculation shear of 1100 $sec^{-1}$ and a volumetric flux of 6 liters per square meter per hour in both stages. The volume of fluid processed was 200 mls and the processing time in each case was about 5 hours.

The feed solution consisted of a 0.25% HSA in phosphate buffered saline was spiked with a phage, in one case Phi X 174 and in the second case Phi 6 each at about $5\times10^7$ $pfu/_{ml}$. Samples were drawn in each stream and the results reported in Tables II and III, the stream numbers referred to in Tables II and III are shown in FIG. **2*d*. The ratio of the measured HSA concentration to that of the starting feed and the virus LRV value in each stream after 5 hours is reported. The HSA concentration ratio is compared with values calculated based upon the rejection coefficients presented in FIG. 4. Concentrations in each stream matches closely the theoretical value indicating HSA recovery in accordance with membrane properties. In the case of Phi X 174, 4.2 log and 4.8 log removal is measured in the effluent of stage 1 and 2 respectively and a total of 5.6 log overall removal measured in the final processed fluid. In the case of Phi 6, no Phi 6 was measured in the effluent of either stage. In both experiments, virus is recovered in stream 31** withdrawn from the first stage recirculation streams.

TABLE II

| Stream | Theoretical HSA Conc | Measured HSA Conc | X174 LRV |
|---|---|---|---|
| 26 | .92 | .89 | 4.2 |
| 38 | .90 | .90 | 4.8 |
| 46 | | | 5.6 |
| 31 | 1.8 | 2.0 | 0.6 |
| 52 | 2.0 | 1.4 | 0.7 |

TABLE III

| Stream | Theoretical HSA Conc | Measured HSA Conc | Phi 6 LRV |
|---|---|---|---|
| 26 | .99 | .89 | >6.5 |
| 38 | .90 | .64 | >6.5 |
| 46 | | | >6.5 |
| 31 | 1.8 | .7 | 0.1 |
| 52 | 2.0 | 1.53 | >6.5 |

We claim:

1. A composite asymmetric membrane designed for selectively separating particles having a size within a size range characteristic of the size of virus particles from a solution containing said particles which comprises a substrate having pores of an average size between about 0.05 and 10 microns, a surface skin and an intermediate porous zone being positioned between said substrate and said skin, said intermediate zone being porous and free of voids which extend from said skin to said membrane substrate, said composite membrane having a protein molecular weight cut-off of between about $5\times10^2$ and $5\times10^6$ Daltons and having properties for producing a log reduction value of at least about 3 and said log reduction value being a monotonically increasing function of particle diameter in the particle size range between about 10 and 100 nanometer diameter.

2. The composite membrane of claim 1 wherein said intermediate porous zone has a thickness between about 5 and 20 microns.

3. The composite membrane of claim 1 wherein the substrate is a microporous membrane.

4. The composite membrane of claim 3 wherein the intermediate porous zone has a thickness between about 5 and 20 microns.

5. The composite membrane of claim 4 wherein the membrane substrate is formed from polyvinylidene difluoride.

6. The composite membrane of any one of claims 1, 2, 3 or 4 in the form of a flat sheet.

7. The composite membrane of any one of claims 1, 2, 3 or 4 in the form of a hollow fiber and wherein said skin comprises an outside surface of said fiber.

8. The composite membrane of any one of claims 1, 2, 3 or 4 having pores with a hydrophilic surface.

9. The composite membrane of claim 3 wherein the membrane substrate is formed from polyvinylidene difluoride.

10. The composite membrane of claim 3 wherein said skin, said intermediate porous zone and said membrane are formed from polyvinylidene difluoride.

11. The composite membrane of any one of claims 9, 5 or 10 having an intermediate zone thickness between about 5 and 10 microns.

12. A process comprising: selectively removing particles of a size between about 10 and 100 nanometers from a solution at a log reduction value of at least about 3 by, in a first filtration step, passing said solution in direct contact with the skin of the composite membrane designed for selectively separating particles having a size within a size range characteristic of the size of virus particles from a solution containing said particles which comprises a substrate having pores of an average size between about 0.05 and 10 microns, a surface skin and an intermediate porous zone being positioned between said substrate and said skin, said intermediate zone being porous and free of voids which extend from said skin to said membrane substrate, said composite membrane having a protein molecular weight cut-off of between about $5 \times 10^2$ and $5 \times 10^6$ Daltons and having properties for producing a log reduction value of at least about 3 and said log reduction value being a monotonically increasing function of particle diameter in the particle size range between about 10 and 100 manometer diameter retaining said particles by said skin sufficient to form a particle-rich solution while allowing solute in said solution substantially free of said particles to pass through said composite membrane sufficient for causing the log reduction value of particle removal is a monotonically increasing function of the diameter of said particles.

13. The process of claim 12 wherein the particles are virus particles and said solution is a protein solution.

14. The process of claim 12 wherein the intermediate porous zone of said membrane has a thickness between about 5 and 20 microns.

15. The process of any one of claims 12, 13 or 14 wherein said composite membrane is in the form of a flat sheet.

16. The process of any one of claims 12, 13 or 14 wherein at least a portion of said particle-rich solution is recycled to directly contact said skin of said composite membrane.

17. The process of any one of claims 12, 13 or 14 wherein said composite membrane is in the form of a flat sheet and at least a portion of said particle-rich solution is recycled to directly contact said skin of said composite membrane.

18. The process of any one of claims 12, 13 or 14 wherein said particle-rich stream is passed, in a second filtration step directly into contact with a skin of a second composite membrane of claim 1 to produce a second particle-rich solution and a second solution substantially free of said particles.

19. The process of any one of claims 12, 13 or 14 wherein said particle-rich stream is passed in a second filtration step directly in contact with a skin of a second composite membrane of claim 1 to produce a second particle-rich solution and a second protein solution substantially free of particles and recycling at least one of said first or second particle-rich solutions to one of said filtration steps.

20. The process of claim 12 wherein the skin, intermediate porous zone and said membrane substrate are formed from polyvinylidene difloride.

* * * * *

UNITED STATES PATENT AND TRADEMARK OFFICE
CERTIFICATE OF CORRECTION

PATENT NO. : 5,017,292
DATED : May 21, 1991
INVENTOR(S) : Anthony J. DiLeo, et al It is certified that error appears in the above-identified patent and that said Letters Patent is hereby corrected as shown below:

Column 12, Line 26, replace $$ \text{"} \quad = \frac{\rho^2 D*^{1/2}}{L^{1/2} h^{3/2}} \cdot \frac{1}{(1+K)^2} \quad \text{"} $$

with $$ - \quad = \frac{^2 D*^{1/2}}{L^{1/2} h^{3/2}} \times \frac{1}{(1+K)^2} $$

Column 12, Line 29, replace
" $\delta$ " with $-\gamma-$

Column 13, Line 22, replace
"$P_c = 2.0D* h^{1/2}/(1+K)^2 L_\rho L\mu^{1/2}$" with $-\Delta_c = 2.0D*h^{1/2}/(1+K)^2 L_\rho L\mu^{1/2}$" $-$ Column 13, Line 24, replace
" $\Delta$ PC" with $-\Delta_c \quad -$ Signed and Sealed this Twenty-second Day of December, 1992

*Attest:*

DOUGLAS B. COMER

*Attesting Officer*   *Acting Commissioner of Patents and Trademarks*